(12) United States Patent
Saul et al.

(10) Patent No.: US 9,535,070 B2
(45) Date of Patent: Jan. 3, 2017

(54) HIGH THROUGHPUT DETECTION OF FUSION PROTEINS

(71) Applicant: Arizona Board of Regents, a body corporate of the State of Arizona, acting for and on behalf of Arizona, Scottsdale, AZ (US)

(72) Inventors: Justin Saul, Mesa, AZ (US); Ji Qiu, Chandler, AZ (US); Joshua LaBaer, Chandler, AZ (US); Mitch Magee, Chandler, AZ (US); John Chaput, Phoenix, AZ (US); Sujay Sau, Mesa, AZ (US)

(73) Assignee: ARIZONA BOARD OF REGENTS, A BODY CORPORATE OF THE STATE OF ARIZONA, ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 14/073,332

(22) Filed: Nov. 6, 2013

(65) Prior Publication Data
US 2014/0141991 A1    May 22, 2014

Related U.S. Application Data

(60) Provisional application No. 61/724,608, filed on Nov. 9, 2012.

(51) Int. Cl.
*G01N 33/58*        (2006.01)

(52) U.S. Cl.
CPC .................. *G01N 33/582* (2013.01)

(58) Field of Classification Search
CPC . C12N 15/62; C12N 15/625; G01N 27/44791; B01L 3/50273
See application file for complete search history.

(56) References Cited

FOREIGN PATENT DOCUMENTS

WO    WO2005038460    *   4/2005

OTHER PUBLICATIONS

Sun et al. ChemBioChem 2011, 12, 2217-2226.*
Kay et al.High Throughput Protein Expression and Purification. Humana Press, 2009. 185-198.*
Gene Expression and Cellular Analysis. New England Biolabs. Accessed Oct. 22, 2012. http://www.neb.com/nebecomm/products/category140.asp?#141.
HaloTag Technology: Focus on Imaging Protocol TM260. Promega Corporation. Accessed Oct. 22, 2012. http://www.promega.com/resources/protocols/technicalmanuals/0/halotag-technology-focus-on-imaging-protocol/2.

(Continued)

*Primary Examiner* — J. Christopher Ball
(74) *Attorney, Agent, or Firm* — Quarles & Brady LLP (57) ABSTRACT

A method and related microfluidic chip and kit for high throughput detection of proteins of interest contained in a sample is disclosed. The method comprises of specifically labeling fusion proteins in a complex sample with fusion tag specific fluorophores that specifically bind the fusion tags coupled to the proteins of interest, and subjecting the sample to automated capillary electrophoresis, wherein the presence of the proteins of interest in the sample is detected by fluorescence signals associated with the fusion tag specific fluorophores.

5 Claims, 11 Drawing Sheets

(56) References Cited

OTHER PUBLICATIONS

Lumio In-Cell Labeling Kits. Life Technologies. Accessed Oct. 22, 2012. http://tools.invitrogen.com/content/sfs/manuals/lumioincell-labeling_man.pdf.
Swap: A High Throughput Automated Microfluidic Alternative to Western Blotting. PerkinElmer Inc. Accessed Oct. 23, 2012. http://www.perkinelmer.com/CMSResources/Images/44-133015APP_SWAP.%20A%20High%20Throughput%20Automated%20Microfluidic%20Alternative%20to%20Western%20Blotting.pdf.
Technical manual, Promega, "HaloTag Interchangeable Labeling Technology"; http://www.promega.com, 2006.

\* cited by examiner

LabChip principle

'Standard' Protocol

1. Denatured, unstained, unlabeled protein sample is sipped into chip (~170 nL)
2. Sample is mixed with a quantification marker (1:2 ratio)
3. Sample enters gel matrix and mixes with LC90 fluorescent dye (+/-)
4. Proteins in sample undergo electrophoretic separation (+/-)
5. Sample is diluted with gel matrix (dye-free)
6. Sample is analyzed with 635/700 nm fluorometer

LC90 Fluorescent HaloTag Ligand Detection

FIG. 9

LC90 Fluorescent HaloTag Ligand Detection

HIGH THROUGHPUT DETECTION OF FUSION PROTEINS

CROSS-REFERENCE TO RELATED APPLICATIONS

This application claims the benefit of U.S. Provisional Application 61/724,608, filed Nov. 9, 2012, which is incorporated herein by reference for all purposes.

STATEMENT REGARDING FEDERALLY SPONSORED RESEARCH

This invention was made with government support under DK093449 awarded by the National Institutes of Health. The government has certain rights in the invention.

FIELD OF THE INVENTION

The present invention generally relates to protein detection. In particular, the invention is related to methods and devices for high throughput detection of fusion proteins with fusion tag-specific fluorescent labels.

BACKGROUND

It is desired to have methods and devices of simultaneous detection and purification of large numbers of proteins of interest (POI). While methods currently exist to specifically detect expression of fusion proteins, they are either not suitable for a high throughput process, i.e. western blots, or are non-qualitative, i.e., ELISAs.

At present, capillary electrophoresis instruments have been adopted to assess protein purity and quantifying yield of hundreds of samples within a few hours. Most of these methods lack the capacity to detect specific POI, making them poorly suited for screening for protein expression within complex samples, such as cell lysates. Consequently, there are limited means to detect fusion protein expression in a high throughput setting, despite the increasing need. It is desirable to have the ability to detect specific expression within lysates which will allow rapid characterization of starting materials as part of a high throughput protein production pipeline.

Needed in the art are methods and devices for high throughput detection and purification of large numbers of proteins of interest by using fusion tag-specific fluorescent labels and electrophoresis techniques.

SUMMARY OF THE INVENTION

In one embodiment, the present invention discloses a method for high throughput detection of proteins of interest with fusion tag specific fluorophores that specifically bind the fusion tags coupled to the proteins of interest, and subjecting the sample to automated capillary electrophoresis, wherein the presence of the proteins of interest in the sample is detected by fluorescence signals associated with the fusion tag specific fluorophores.

In another embodiment, the present invention discloses a method for high throughput detection, or assay of a protein, which applies to the complex protein samples of a cell lysate.

In another embodiment, the present invention discloses a method for high throughput detection, or assay of a protein, which comprises a high throughput technique of automated capillary electrophoresis technique, such as a microfluidic chip.

DESCRIPTION OF THE INVENTION

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising" and variations thereof do not have a limiting meaning where these terms appear in the description and claims. Accordingly, the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

As used herein, the term "fusion protein" refers to proteins created through the joining of two or more genes which originally coded for separate proteins. Translation of this fusion gene results in a single polypeptide with functional properties derived from each of the original proteins. Recombinant fusion proteins may be created artificially by recombinant DNA technology for use in biological research or therapeutics. Often for affinity purification, the gene for an affinity tag is combined with the gene for a protein of interest, in order to express the protein of interest fused to an affinity tag.

As used herein, the term "high-throughput detection" or "high-throughput screening" refers to a method for scientific experimentation especially used in drug discovery and relevant to the fields of biology and chemistry. Using robotics, data processing and control software, liquid handling devices, and sensitive detectors, high-throughput screening may allow a researcher to quickly conduct millions of chemical, genetic or pharmacological tests. Through this process one can rapidly identify active compounds, antibodies or genes which modulate a particular biomolecular pathway. The results of these experiments may provide starting points for drug design and for understanding the interaction or role of a particular biochemical process in biology.

As used herein, the term "enzyme-linked immunosorbent assay (ELISA)" refers to a test that uses antibodies and color change to identify a substance. ELISA is a popular format of a "wet-lab" type analytic biochemistry assay that uses a solid-phase enzyme immunoassay (EIA) to detect the presence of a substance, usually an antigen, in a liquid sample or wet sample. The ELISA may be used as a diagnostic tool in medicine and plant pathology, as well as a quality-control check in various industries.

As used herein, the term "affinity label" refers to a substance, molecule or biomolecule, which binds rapidly, and irreversibly to the protein of interest to form a "fusion tag" or a "affinity tag", by a means, e.g., expression, and which is further capable of specifically binding to a fluorescent label.

As used herein, the terms "fluorescent label", "fluorophore", "dyes", and "fluorescent molecule" have the same or similar meaning in the invention and are interchangeable throughout the invention. For example, the term "fluorophore", "fluorochrome", or "chromophore", as used herein, refers to a fluorescent chemical compound that can re-emit light upon light excitation. Fluorophores may typically contain several combined aromatic groups, or plane or cyclic molecules with several $\pi$ bonds.

Fluorophores may sometimes be used alone, as a tracer in fluids, as a dye for staining of certain structures, as a substrate of enzymes, or as a probe or indicator (when its fluorescence is affected by environment such as polarity, ions, et. al.). But more generally fluorophore may be covalently bonded to a macromolecule, serving as a marker (or dye, or tag, or reporter) for affine or bioactive reagents (antibodies, peptides, nucleic acids, et. al.). Fluorophores may notably be used to stain tissues, cells, or materials in a variety of analytical methods, i.e. fluorescent imaging and spectroscopy.

Figure 1:
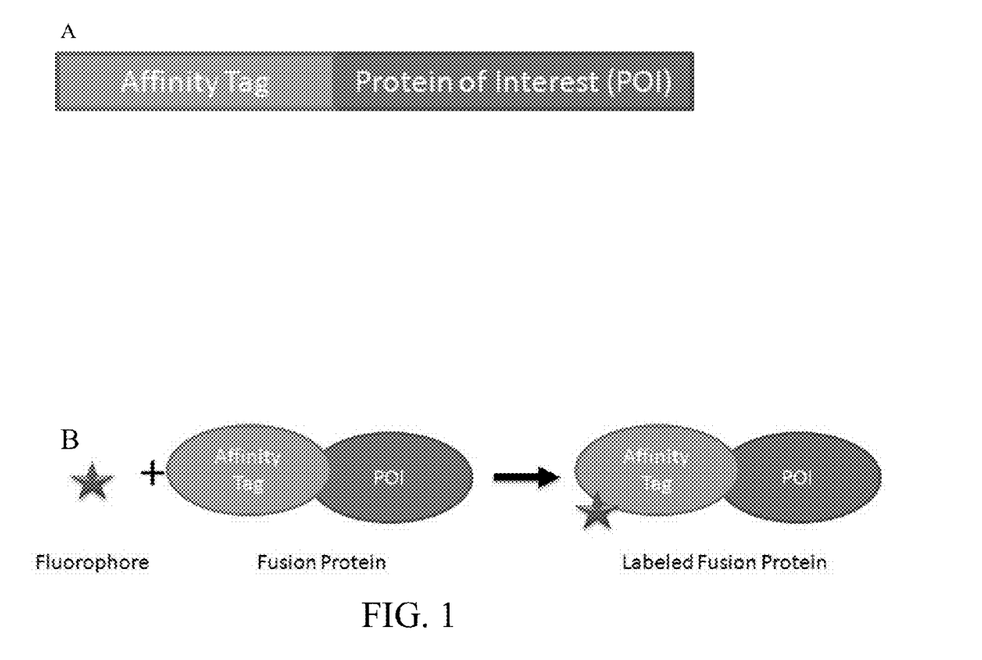
FIG. 1 is a schematic diagram depicting a general structure of protein of interest (POI) expressed as fusion proteins with an affinity tag (FIG. 1A) and the reaction of the affinity tag binding to a fluorescent label (fluorophore) when folded correctly (FIG. 1B).

In one embodiment, the present invention relates to proteins of interest (POI) expressed as fusion proteins including an affinity tag, which further specifically binds to a fluorescent label. FIG. 1 shows a general concept of fusion protein expression with an affinity tag. The POI were initially expressed as fusion proteins including an affinity tag. The expression of such fusion proteins employs techniques of molecular biology that are well known to those skilled in the art and consist of, e.g., recombinant protein expression and any other suitable techniques.

The affinity tag may be any molecules or biomolecules which are capable of specifically linking to one fluorescent molecule as the fluorophore (fluorescent label). Specifically, the affinity tag may be proteins having suicidal enzymatic activity, also called suicide enzymes. Suicide enzymes are proteins whose enzymatic activity is modified by specific mutations allowing them to bind a substrate rapidly, covalently, and irreversibly, as these enzymes can each bind only one fluorescent molecule, and the further binding activity of the enzyme is blocked by the binding of the substrate.

The fluorophore or fluorescent label may be any fluorescent molecules or dyes. Specifically, the fluorophore or fluorescent label may be a dye compatible with the fluorescent detection equipment being used. Some examples of these dyes may be seen below. All of these dyes may be commercially available as fluorescent substrates for fusion tags, and each binds covalently to a different tag. Most developed fusion tags may have many fluorescent variations of the ligand to cover a broad portion of the UV spectrum. Any suitable fluorescent molecules or dyes may be used for the present invention. In a preferred embodiment of the present invention, a microfluidic system such as LabChip systems (available from Caliper) may be equipped with a 635 nm excitation light source, and a 700 nm emission filter, making dyes with excitation and emission maxima near these wavelengths ideal choices when selecting a fluorophore for use on a LabChip system. Any fluorescent molecules or dyes having suitable excitation and emission maxima near the required wavelength may be used for the present invention.

For example, an Alexa660 fluorophore meets these criteria, although other fluorophores are likely to work as well. Examples of available fluorescent dyes or fluorophores may include those covalently bind to fusion tags. Dyes or fluorophores with excitation and emission maxima near 635 and 700 nm are expected to be compatible with LabChip systems.

The examples of fluorophores may include HaloTag Alexa Fluor 488 Ligand as shown below (available from PROMEGA). HaloTag Alexa Fluor 488 Ligand has maxima excitation and emission at 499/518 nm (ex/em). As comparison, the excitation and emission maxima for Alexa660 are 654/690 nm (ex/em).

The examples of fluorophores or dyes may also include SNAP-Cell 505 (available from NEB), as shown below. SNAP-Cell 505 has its excitation and emission maxima at 504/532 nm (ex/em). The structure of SNAP-Surface Alexa Fluor 647 (not shown) and its excitation and emission maxima are 652/670 nm (ex/em).

The examples of fluorophores or dyes may also include CLIP-Surface 647 (available from NEB), and it has its excitation and emission maxima at 635/650 nm (ex/em).

The examples of fluorophores or dyes may further include Lumio-Red (available from LIFE TECHNOLOGIES), and it has excitation and emission maxima at 593/608 nm (ex/em).

In one embodiment, the affinity tag may be SNAP-tag (marketed by COVALYS), a mutant of an alkylguanine-DNA alkyltransferase, and one of the substrates for SNAP-tag is benzylguanine.

Figure 2:
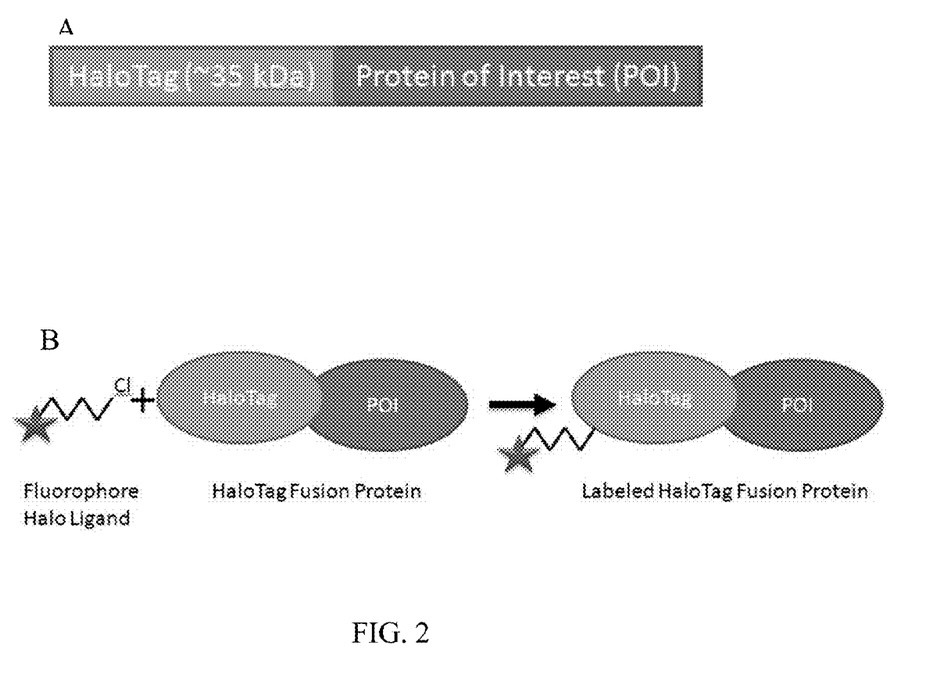
FIG. 2 is a schematic diagram showing an example of protein of interest (POI) expressed as HaloTag fusion proteins including an affinity tag (FIG. 2A) and the reaction of HaloTag covalently binding to a chloroalkane ligand when folded correctly (FIG. 2B). The chloroalkane ligand can be functionalized with a fluorescent label (fluorophore) for detection (FIG. 2B).

In one preferred embodiment of the present invention, the affinity tag may be HaloTag (marketed by PROMEGA), a mutant of a dehalogenase, and some of substrates for HaloTag are compounds of the chloroalkane family. The native enzyme of HaloTag is DhaA, a monomeric protein (MW≈33 KDa), which breaks carbon halogen bonds in aliphatic halogenated compounds. Upon nucleophilic attack of Asp106 in the enzyme carbon-halogen bonds of chloroalkane, an ester bond is formed between fluorophore HaloTag ligand and the enzyme. HaloTag may contain a critical mutation from His272 to Phe in the catalytic triad so that the produced ester bond between the enzyme and the ligand can not be further hydrolyzed (Technical manual, Promega, "HaloTag Interchangeable Labeling Technology"; http://www.promega.com, 2006). FIG. 2 shows that HaloTag may be used as an affinity tag for the expression of proteins of interest (POI) into HaloTag fusion proteins (FIG. 2A). As shown in FIG. 2B, HaloTag in the fusion proteins may further covalently bind a chloroalkane fluorophore HaloTag ligand by cleaving the carbon-chloride bond in the ligand. The binding process between fusion proteins and fluorescent HaloTag ligand requires that HaloTag be correctly folded.

Figure 3:
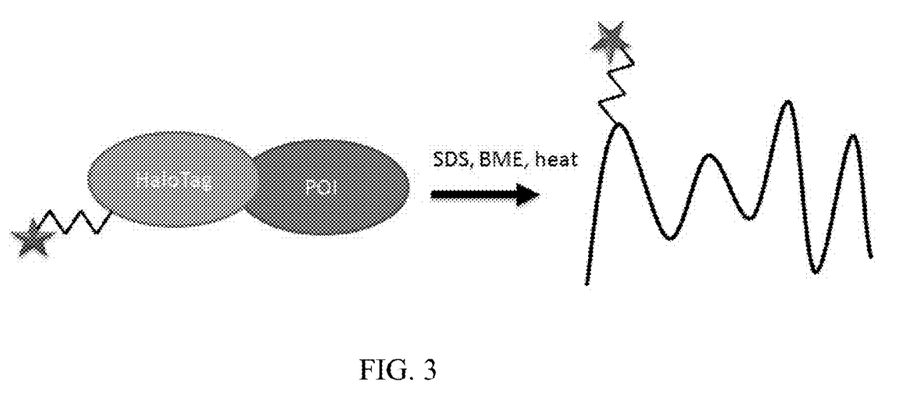
FIG. 3 is a schematic diagram showing that the fluorescent label will remain bound to the HaloTag fusion protein after denaturation and electrophoresis.

Further, as shown in FIG. 3, the resulting fluorescent label having a covalent bond between HaloTag in the fusion proteins and the ligand may remain bound to the HaloTag fusion protein after denaturation and electrophoresis. These observations indicate that binding between the ligands and the fusion tag is permanent, allowing denaturation of the protein to perform electrophoresis and assay molecular weight.

Figure 4:
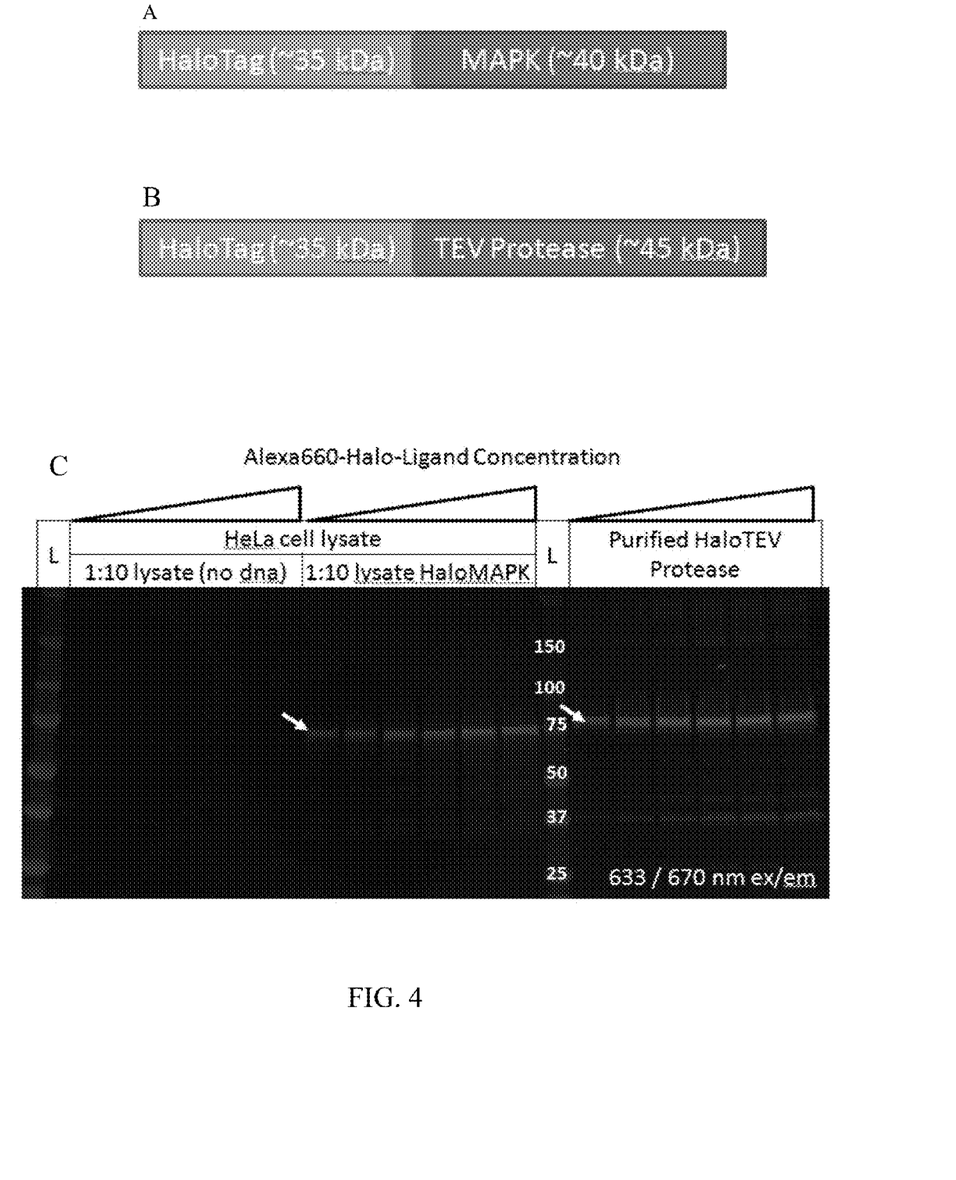
FIG. 4 depicts sodium dodecyl sulfate polyacryamide gel electrophoresis (SDS-PAGE) analysis visualized through the fluorescent label (fluorophore) of Alexa660 (emission at 670 nm) following 633 nm light excitation showing gel-based detection of two HaloTag fusion protein examples of Halo-MAPK (FIG. 4A) and HaloTEV (FIG. 4B) in the presence of different concentrations of Alexa660-Halo-ligand (for each category of the protein, the concentrations of Alexa660-Halo-ligand increases from left to right) in lysate.

In one embodiment, the present invention relates to methods of detection of HaloTag fusion proteins in lysate. The HaloTag fusion proteins including a fluorescent label may be detected by using a gel-based detection technique. Any gel-based detection techniques may be suitable for the present invention. In one preferred embodiment, the gel-based detection techniques may be SDS-PAGE. FIG. 4 shows a graph of sodium dodecyl sulfate polyacryamide gel electrophoresis (SDS-PAGE) analysis on the detection of HaloTag fusion proteins in lysate. Two HaloTag fusion proteins were investigated including Halo-MAPK (FIG. 4A) and HaloTEV (FIG. 4B). Halo-MAPK (FIG. 4A) includes a HaloTag protein (~35 kDa) and a MAPK protein (~40 kDa), showing a total molecular weight of ~75 kDa. HaloTEV (FIG. 4B) includes a HaloTag protein (~35 kDa) and a TEV protease (~45 kDa), showing a total molecular weight of ~80 kDa. Alexa660 was used as the fluorescent label (fluorophore) for both fusion proteins of Halo-MAPK and HaloTEV. The fusion proteins were visualized through the fluorescent label (fluorophore) of Alexa660 (emission at 670 nm) following 633 nm light excitation.

The HaloTag fusion proteins in a complex protein mixture, may be detected directly by the gel-based techniques. As shown in FIG. 4, the fusion protein of Halo-MAPK (1:10 lysate) was clearly visualized, which was confirmed with the total molecular weight mark at ~75 kDa. Further, with increasing concentrations of Alexa660-Halo-ligand (from left to right), the fusion protein of Halo-MAPK showed an increasing intensity of detection. As a comparison, in the absence of the corresponding DNA, lysate Halo-MAPK can not be detected.

Alternatively, HaloTag fusion proteins may be detected after the fusion proteins were purified. As shown in FIG. 4, the purified HaloTEV protease was clearly visualized, which was confirmed with the total molecular weight mark at ~80 kDa. Further, with increasing concentrations of Alexa660-Halo-ligand (from left to right), the fusion protein of HaloTEV showed an increasing intensity of detection.

Figure 5:
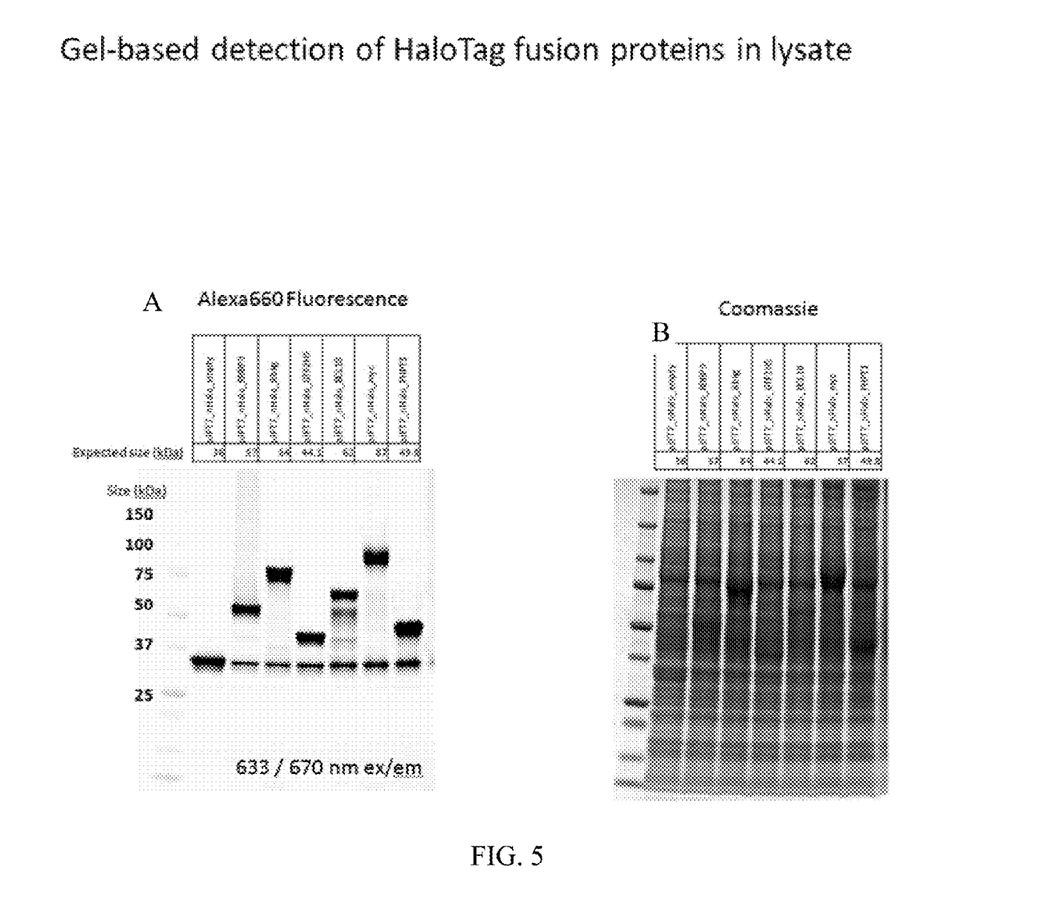
FIG. 5 depicts sodium dodecyl sulfate polyacryamide gel electrophoresis (SDS-PAGE) analysis showing gel-based detection of various fusion protein examples including HaloTag and the fluorescent label (fluorophore) of Alexa660 (FIG. 5A) or Coomassie (FIG. 5B). While that using Alexa660 showed distinctive detections of various fusion proteins, the method using Coomassie showed less distinctive detections of the targeting fusion proteins.

Further, gel-based detection techniques on HaloTag fusion proteins in lysate may show suitable sensitivity of detection with various molecular weight (size) of the fusion proteins. Reference is now made to FIG. 5, which shows sodium dodecyl sulfate polyacryamide gel electrophoresis (SDS-PAGE) analysis on HaloTag fusion protein examples, having various molecular weights. As shown in FIG. 5A, when Alexa660 was used as the fluorescent label, the HaloTag fusion proteins, having molecular weight in the range of 30-90 kDa, were distinctively detected. Visualized through the fluorescent label (fluorophore) of Alexa660 (emission at 670 nm) following 633 nm light excitation, the HaloTag fusion proteins showed distinct bands of detection corresponding to their molecular weights. As shown in FIG. 5B, total protein staining with coomassie reveals the high protein complexity of the lysate and the relatively low abundance of the HaloTag fusion proteins. The fluorescent analysis much more clearly indicates successful expression of the fusion proteins than coomassie staining (FIG. 5A).

Various protocols of gel-based detection on fusion proteins in lysate have already been published or marketed using gel-based fluorescent detection of covalently bound fluorophores to affinity tags. The commercially available products include, e.g., HaloTag from Promega, Lumio Tag from Life Technologies, and SNAP/CLIP Tags from NEB. Nevertheless, the gel-based detection protocols show many limitations. For instance, gel-based detection protocols are not high throughput technologies. Consequently, these gel-based detection protocols are commonly applied to small scale problems.

While there is an increasing need for high throughput detection of fusion proteins in lysate, automated capillary electrophoresis represents one of the potential high throughput alternatives to traditional PAGE analysis. Caliper is the primary manufacturer of automated capillary electrophoresis instruments/chips. Caliper's LabChip systems are the industry standard for high throughput expression/purification characterization. LabChip, as a microfluidic lab-on-a-chip technology, represents a significant advancement in laboratory experimentation, bringing the benefits of miniaturization, integration and automation to numerous research-based industries. Nevertheless, LabChip instruments utilize a fluorescent protein stain that detects all proteins non-specifically.

Figure 6:
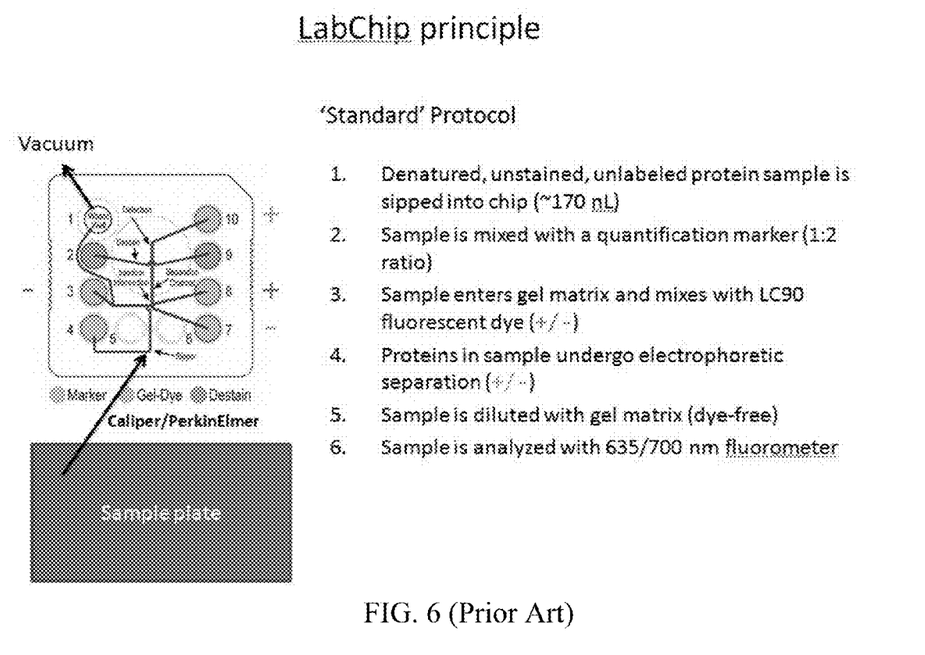
FIG. 6 is a systematic diagram showing a typical LabChip setup from Caliper/Perkin Elmer along with the standard experimental protocol of the LabChip setup (adapted from PerkinElmer's website). Automated capillary electrophoresis is the high throughput alternative to traditional PAGE analysis. These instruments commonly utilize a fluorescent protein stain that detects all proteins non-specifically.

FIG. 6 shows a typical LabChip setup from Caliper/PerkinElmer along with the standard experimental protocol. As shown in FIG. 6, a standard LabChip protein separation protocol includes: 1) Denatured, unstained, unlabeled protein sample is sipped into chip (~170 nL); 2) Sample is mixed with a quantification marker (1:2 ratio); 3) Sample enters gel matrix and mixes with LC90 fluorescent dye (3 and 8; +/−); 4) Proteins in sample undergo electrophoretic separation (7 and 10; +/−); 5) Sample is diluted with gel matrix (dye-free); 6) Sample is analyzed with 635/700 nm fluorometer.

Figure 7:
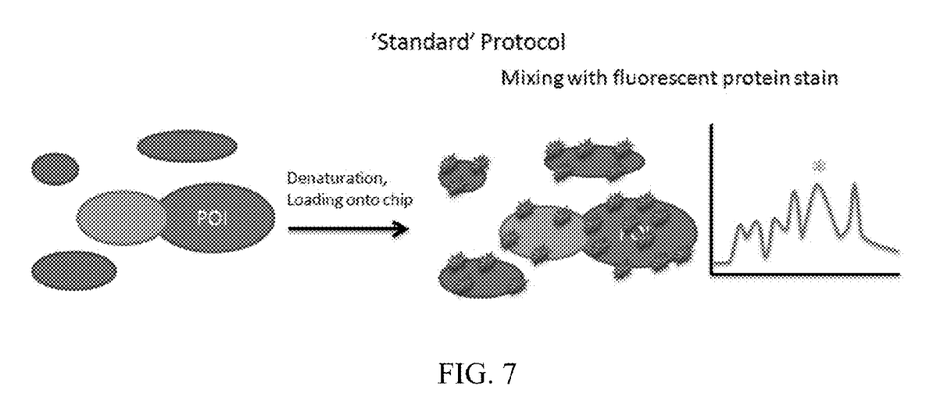
FIG. 7 is a schematic diagram showing the standard protein detection protocol of LabChip setups where these setups commonly utilize a fluorescent protein stain that detects all proteins non-specifically.

Although automated capillary electrophoresis such as using LabChip is the potential high throughput alternative to traditional PAGE analysis, the commonly available instruments of LabChips utilize a fluorescent protein stain that detects all protein non-specifically. As shown in FIG. 7, due to the non-specific binding ability of the fluorescent protein stain, after denaturation and loading the samples of proteins into the chip, all the proteins including proteins of interest (POI) and all other proteins would be labeled with the non-specific fluorescent protein stain. Consequently, in the resulting spectra, the signal of POI would be buried in the signals from the other undesired proteins.

In one preferred embodiment, the present invention relates to high throughput detection methods and devices by combining a high throughput automated capillary electrophoresis technique such as the LabChip technology with fusion tag detections. The tag molecule may be any molecules or biomolecules, which are capable of specifically binding to a fluorescent molecule. The examples may include SNAP-tag, CLIP, Lumio Tag, or HaloTag. Even though HaloTag has been described during the following examples and embodiments, a person having ordinary skill in the art will understand that any other tag molecules may be used for the present invention.

Further, even though LabChip technology has been used during the following examples and embodiments, a person having ordinary skills in the art will understand that any high throughput automated capillary electrophoresis techniques may be used for the present invention.

Figure 8:
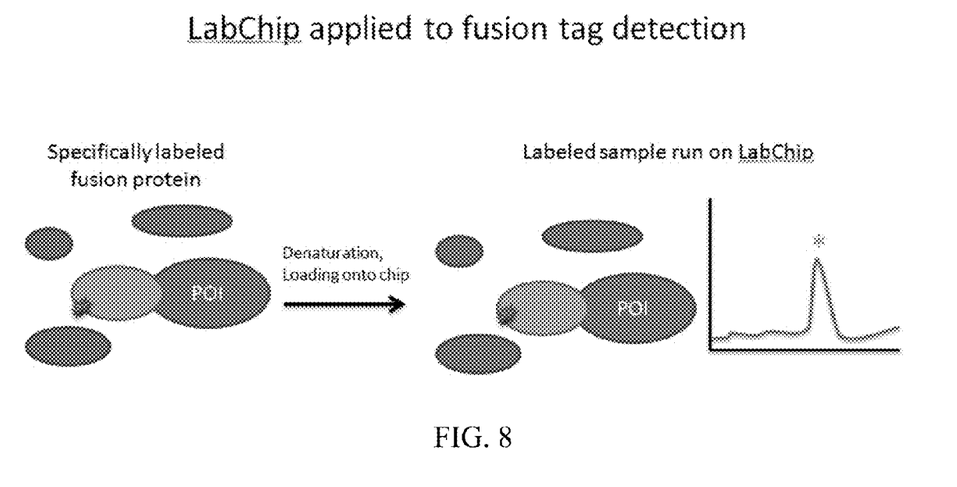
FIG. 8 is a schematic diagram showing the protocol of the present invention with LabChip applied to fusion tag detection where specifically labeled fusion proteins lead to a specific detection only on the labeled samples on LabChip.

As shown in FIG. 8, an additional step of mixing the proteins with non-fluorescent protein stains is not needed for the fusion protein detection protocol, as the fusion protein including POI has been specifically labeled. Thus, after denaturation and loading the proteins into the chip, only the labeled fusion protein including POI will be detected as it is the only fluorescence-labeled protein. Consequently, the resulting spectra would only exhibit the signal of the desired protein as shown in FIG. 8. The much cleaner signal detection corresponding to POI enables the present invention as a high throughput detection technique.

Figure 9:
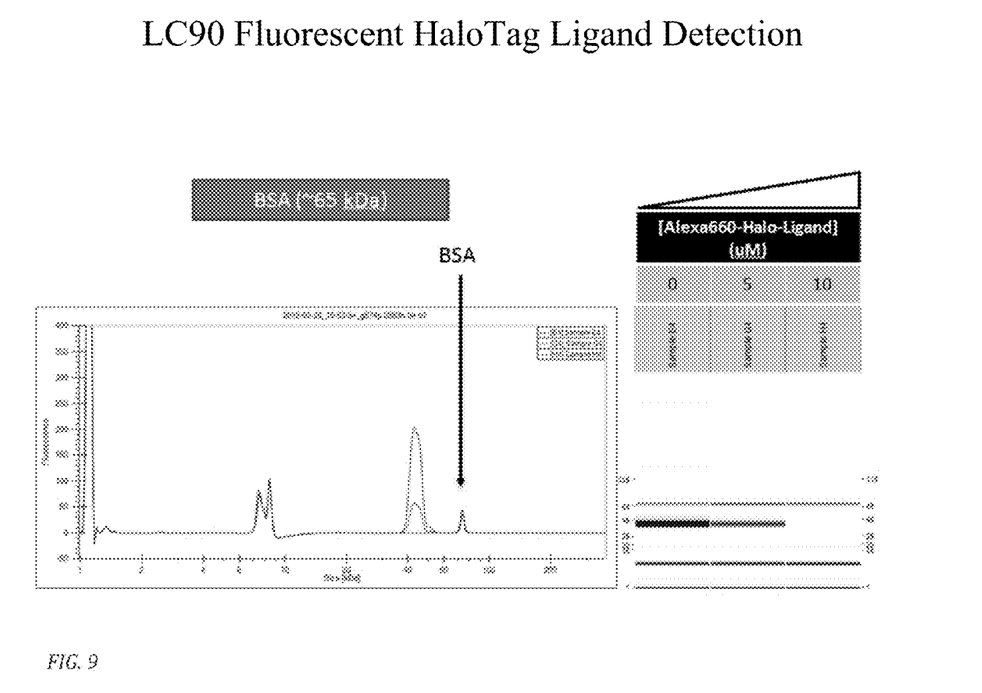
FIG. 9 depicts LC90 fluorescent HaloTag ligand detection in the presence of Bovine serum albumin (BSA; ~65 kDa) using the LabChip setup. Since BSA does not react with the HaloTag ligand, the observed BSA signal is constant with varying Alexa660-Halo-Ligand concentrations.

To further confirm the feasibility of a combination of LabChip with fusion tag detection technique, a controlled experiment was conducted for the detection of Bovine serum albumin (BSA) in the presence of LC90 fluorescent HaloTag ligand (Alexa660-Halo-ligand). As BSA lacks a HaloTag fusion, BSA is not expected to react with the fluorescent HaloTag ligand. As shown in FIG. 9 the peak detected at 65 kDa is consistent with the molecular weight of BSA. Further, the intensity of BSA peak at 65 kDA (FIG. 9; left) and the signal in Gel (FIG. 9; right) remain unchanged with the increasing concentrations of Alexa660-Halo-Ligand. These observations confirm the unreactivity between a non HaloTag fusion protein and HaloTag ligand.

Figure 10:
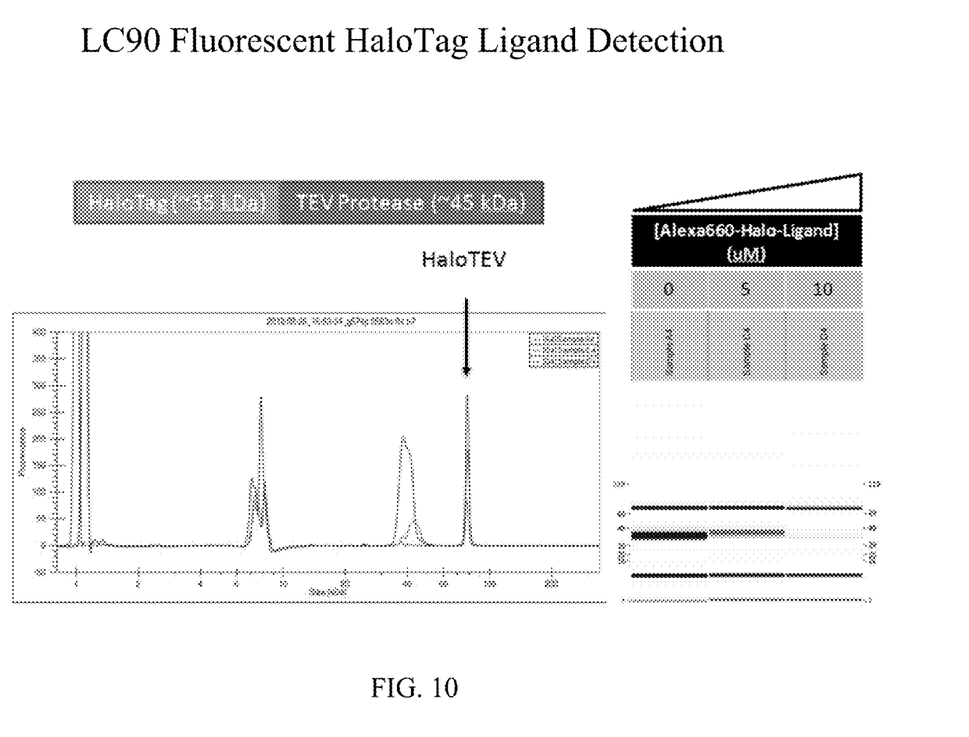
FIG. 10 depicts LC90 fluorescent HaloTag ligand detection on the fusion protein of HaloTEV using the LabChip setup. Due to the formation of fusion protein of HaloTEV, the observed signal of HaloTEV increases with the increasing concentrations of Halo ligand.

To confirm that a combination of LabChip with fusion tag protocols will qualitatively and quantitatively assay and detect proteins in complex samples using high throughput LabChip technique, a detection experiment for the fusion protein of HaloTEV was conducted. FIG. 10 shows the spectra (left) and the corresponding gel signals (right) of a LC90 fluorescent HaloTag ligand detection on the fusion protein of HaloTEV using the LabChip setup. As discussed above, HaloTEV includes a HaloTag protein (~35 kDa) and a TEV protease (~45 kDa), showing a total molecular weight of ~80 kDa. Alexa660 was used as the fluorescent label (fluorophore) for HaloTEV. As shown in FIG. 10 (left), the fusion protein of HaloTEV was detected at 80 kDa, consistent with its total molecular weight. More importantly, as the concentration of Alexa-Halo-Ligand increases, the intensity of the HaloTEV peak at 80 kDa was enhanced proportionally (FIG. 10; left). These observations indicate that the combination of LabChip with fusion tag protocols can not only qualitatively but also quantitatively assay and detect proteins. The corresponding gel signals (FIG. 10; right) are consistent with these observations.

Further, as the observed fusion proteins show sharp and narrow peaks during these detections (FIGS. 9 and 10), the present invention of a combination of LabChip with fusion tag protocols can be applied to assay, detect, and purify proteins in complex samples such as lysates. Fusion proteins in expression mixtures can be qualitatively and quantitatively detected without prior purification in a high throughput fashion. The high throughput capability of the LabChip techniques enables the present invention to detect large numbers of proteins of interest (POI), thus allowing for a collection of proteins to be detected with a unified method rather other labor-intensive methods such as an individual method for each POI.

Although companies such as Caliper have described an immune precipitation technology, the present invention have many advantages over the previous technology. This approach allows for rapid high throughput screening of expression without the need for antibodies. The present approach may also be applied to strong non-covalent bond interactions such as that between biotin and streptavidin tag as long as the binding strength can withstand downstream analysis protocols.

Additionally, the current approach directly labels fusion proteins with a fusion tag specific fluorophore, and the present invention uses a capillary electrophoresis instrument to specifically detect fusion proteins within complex samples. The present invention also utilizes fusion tags that are able to bind to their specific ligands with high affinity, such as SNAP-tag, CLIP-tag, Halo Tag, Lumio Tag, and others.

In terms of comparing to existing technologies (e.g., Proteinsimple™), the present invention offers at least the following advantages: (a) the present invention can be used on an unmodified LabChip GX or GXII system, and there is no need to purchase a new instrument dedicated to high throughout specific protein detection; (b) the present invention is much faster (~1 hour per plate) than, e.g., the Proteinsimple™'s system (up to 19 hours per plate); (c) the present invention doesn't require antibodies; and (d) the present invention can be used in conjunction with the normal operation of LabChip's protein detection kits, which is thus capable of comparing specific fusion protein signals with total protein signals.

In one aspect, the present invention discloses a method for high throughput detection of proteins of interest contained in a sample. The method comprises the steps of (a) contacting a sample comprising proteins of interest coupled to fusion tags with fusion tag specific fluorophores that specifically bind the fusion tags coupled to the proteins of interest; and (b) subjecting the sample to automated capillary electrophoresis, wherein the presence of the proteins of interest in the sample is detected by fluorescence signals associated with the fusion tag specific fluorophores.

The present invention may generally be applied to high throughput detection of proteins of interest contained in any suitable samples. In one specific embodiment in the present invention, the sample may be a cell lysate, more specifically, a bacterial cell lysate.

Any suitable fusion tag may be used for the present high throughput detection of proteins of interest contained in a sample. In one specific embodiment, the suitable fusion tag may be a fusion tag protein.

In one embodiment, the fusion tags may specifically link to fusion tag specific fluorophores, which may be specifically coupled to the proteins of interest. Any suitable means of linking may be used to connect the fusion tags, fusion tag specific fluorophores and the proteins of interest. In one specific embodiment, the fusion tags, fusion tag specific fluorophores and the proteins of interest may be linked through chemical bonds, such as covalent bonds. Any suitable chemical bonds may be used for the present invention.

In one embodiment of the present invention, any fluorophores may be used as the fusion tag specific fluorophores. In one specific embodiment, the fusion tag specific fluorophore may have an excitation and emission maxima near the specifically required wavelength, such as about 635 nm for excitation and about 700 nm for emission.

In one specific embodiment of the present invention, the suitable fusion tag may be a fusion tag protein which are commercially available, such as SNAP-tag, CLIP-tag, Lumio tag, or HaloTag.

In one embodiment of the present high throughput detection of proteins of interest contained in a sample, the automated capillary electrophoresis may be carried out on a microfluidic chip.

In one aspect, the present invention provides a microfluidic chip for use in a method of high throughput detection of proteins of interest contained in a sample according to any of the above methods.

In another aspect, the present invention provides a kit. The kit comprises a microfluidic chip for use in a method of high throughput detection of proteins of interest contained in a sample according to any of the above methods; a fusion tag specific fluorophore; and a means for detection, wherein the presence of the proteins of interest in the sample is detected by fluorescence signals associated with the fusion tag specific fluorophores.

In one specific embodiment of the kit, the fusion tag specific fluorophore has an excitation and emission maxima near about 635 nm and about 700 nm, respectively.

EXAMPLES

Example 1

Formation of fusion proteins containing affinity tag and proteins of interest. HaloTag was used as an example affinity tag for all the Examples. However, a person having ordinary skill in the art will understand that any suitable affinity tags will work for the purpose of the present invention. Proteins of interest (POI) were expressed as HaloTag fusions following the following steps. Genes were inserted into an appropriate expression vector that encodes either an N-terminal or C-terminal HaloTag fusion partner. For E. coli expression, the expression vector pCPD_nHalo containing the gene was transformed into E. coli strain BL21 (DE3). A 2 mL culture can be grown in LB media with 50 ug/mL ampicilin at 37° C. until $OD_{600}$=0.6, and induced with 1 mM IPTG. Expression for 20 hours at 18° C. was sufficient to produce the HaloTag fusion protein. The culture was pelleted by centrifugation at 5000×g for 20 minutes, and resuspended in a standard lysis buffer containing lysozyme and DNase. After 30 minutes of lysis, the lysate can be analyzed for expression of the fusion protein.

For cell-free expression systems, the expression vector DNA was added to the lysate, and expression can be performed following the kit manufacturer's instructions.

Lysate from either in vivo or in vitro expression systems can be assayed by incubating the lysate with a small concentration of fluorescent HaloTag ligand. A 4 uM stock solution can be added to each sample to make the final concentration 1 uM. Samples can be incubated for 20 minutes and room temperature, and then denatured with SDS and boiling. For testing on a LabChip system, samples can be prepared following manufacturer's instructions.

Example 2

High-throughput detection of HaloTag fusion proteins in lysate using LabChip. The HaloTag fusion proteins were produced following the same procedure as described in Example 1. LabChip system was purchased from Caliper, and no modifications were performed on the system. The experiment follows an automated protocol according to the technical manual of LabChip.

Example 3

Figure 11:
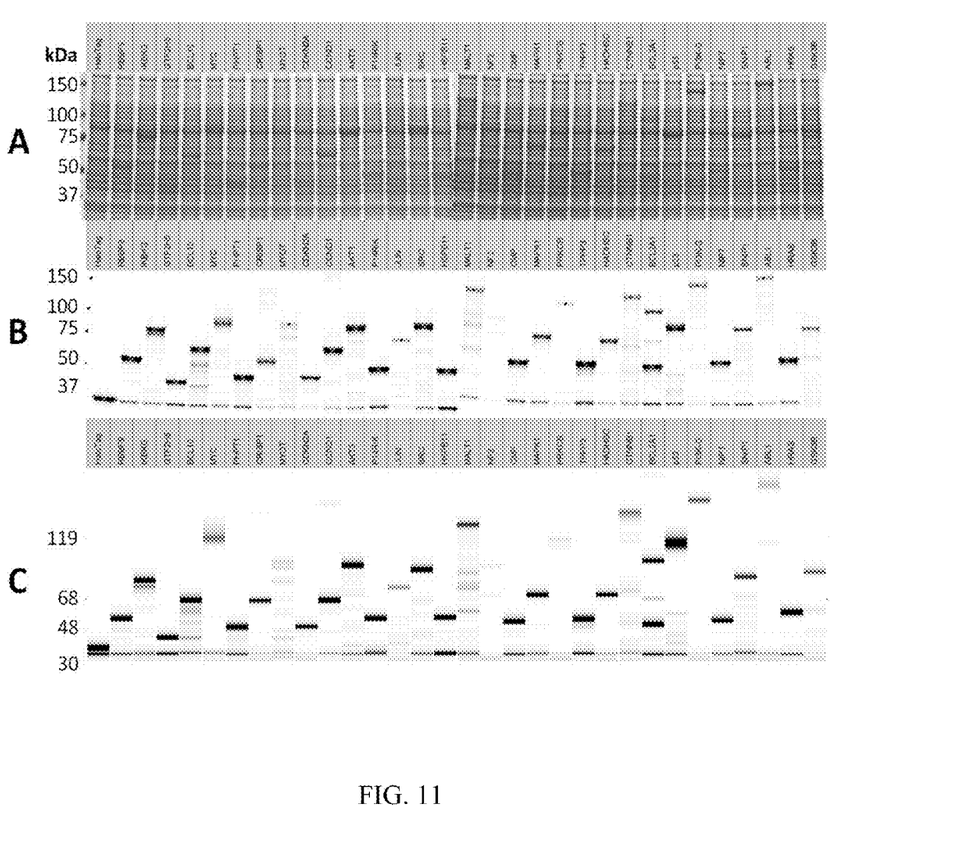
FIG. 11 depicts 32 proteins expressed as N-terminal HaloTag fusion proteins in HeLa cell lysate and incubated with HaloTag-Alexa660 ligand. Expression reactions were denatured and separated by PAGE. (A) Coomassie stain of 1 uL expression reactions; (B) In-gel fluorescence of the same gels prior to Coomassie staining; (C) LabChip virtual gel of collection.

FIG. 11 depicts 32 proteins expressed as N-terminal HaloTag fusion proteins in HeLa cell lysate and incubated with HaloTag-Alexa660 ligand. Expression reactions were denatured and separated by PAGE. (A) Coomassie stain of 1 uL expression reactions; (B) In-gel fluorescence of the same gels prior to Coomassie staining; (C) LabChip virtual gel of collection.

REFERENCES

1. HaloTag Technology: Focus on Imaging Protocol TM260. Promega Corporation. Accessed Oct. 22, 2012. http://www.promega.com/resources/protocols/technical-manuals/0/halotag-technology-focus-on-imaging-protocol/2.
2. HaloTag Technology. Promega Corporation. Accessed Oct. 22, 2012. http://www.promega.com/~/media/images/product%20marketing%20pages/product%20marketing%20images/halotag%20technology/halotag-web-banner.jpg?la=en&w=600&h=150&as=1
3. Gene Expression and Cellular Analysis. New England Biolabs. Accessed Oct. 22, 2012. http://www.neb.com/nebecomm/products/category140.asp?#141
4. Lumio In-Cell Labeling Kits. Life Technologies. Accessed Oct. 22, 2012. http://tools.invitrogen.com/content/sfs/manuals/lumioincelllabeling_man.pdf
5. SWAP: A High Throughput Automated Microfluidic Alternative to Western Blotting. PerkinElmer Inc. Accessed Oct. 23, 2012. http://www.perkinelmer.com/CMSResources/Images/44-133015APP_SWAP.%20A%20High%20Throughput%20Automated%20Microfluidic%20Alternative%20to%20Western%20Blotting.pdf
6. Technical manual, Promega, "HaloTag Interchangeable Labeling Technology"; http://www.promega.com, 2006

We claim:

1. A method for high throughput detection of proteins of interest contained in a sample, comprising:
    (a) contacting a sample not subjected to prior purification comprising contaminating proteins without fusion tags and affinity tagged fusion proteins of interest to a plurality of fluorescent labels having specificity for the affinity tags, wherein, upon contacting, fluorescent labels covalently bind the affinity tags to form detectable protein complexes;
    (b) subjecting the contacted sample to microfluidic electrophoresis, wherein the presence of the proteins of interest but not contaminating proteins in the contacted sample is detected by fluorescence signals associated with the affinity tags.

2. The method of claim 1, wherein the sample not subjected to prior purification is a cell lysate.

3. The method of claim 1, wherein the sample not subjected to prior purification is a bacterial cell lysate.

4. The method of claim 1, wherein the fusion tag is a fusion tag protein.

5. The method of claim 1, wherein the fusion tag specific fluorophore has an excitation and emission maxima near about 635 nm and about 700 nm, respectively.

* * * * *